United States Patent [19]

Kowalczik et al.

[11] Patent Number: 4,950,808
[45] Date of Patent: Aug. 21, 1990

[54] PROCESS FOR THE PREPARATION OF 4,4'-DIHYDROXYBIPHENYL

[75] Inventors: Udo Kowalczik, Bochum; Martin Bartmann, Recklinghausen; Juergen Finke, Marl, all of Fed. Rep. of Germany

[73] Assignee: Huels Aktiengesellschaft, Marl, Fed. Rep. of Germany

[21] Appl. No.: 341,717

[22] Filed: Apr. 21, 1989

[30] Foreign Application Priority Data

Jun. 11, 1988 [DE] Fed. Rep. of Germany ....... 3819963

[51] Int. Cl.$^5$ ...................... C07C 37/50; C07C 39/12
[52] U.S. Cl. ................................... 568/730; 568/722; 568/723; 568/805
[58] Field of Search ..................... 568/722, 730, 805

[56] References Cited

U.S. PATENT DOCUMENTS 4,205,187  5/1980  Cardenes et al. .................. 568/805
4,482,755  11/1984  Kruse et al. ........................ 568/730

FOREIGN PATENT DOCUMENTS 1011626  4/1983  U.S.S.R. ............................. 568/730

OTHER PUBLICATIONS

Hay "Chemical Abst." vol. 64, p. 6537, (1966).

Primary Examiner—Werren N. Lone
Attorney, Agent, or Firm—Oblon, Spivak, McClelland, Maier & Neustadt

[57] ABSTRACT

Reducing 3,3', 5,5'-tetra-t-butyldiphenoquinone with 2,6-di-t-butylphenol, in the melt, in the presence of a 4-dialkylaminopyridine, and then dealkylating the intermediate formed, in the melt, by adding a phosphorus-containing acid or its derivative provides 4,4'-dihydroxybiphenyl of high purity in high yield.

6 Claims, No Drawings

PROCESS FOR THE PREPARATION OF 4,4'-DIHYDROXYBIPHENYL

BACKGROUND OF THE INVENTION

1. Field of the Invention

The present invention relates to a process for the preparation of 4,4'-dihydroxybiphenyl.

2. Discussion of the Background 4,4'-Dihydroxybiphenyl is useful, for example, for the production of liquid crystalline polyesters.

A number of procedures for the preparation of 4,4'-dihydroxybiphenyl are known. One method consists of first sulfonating biphenyl and then saponifying it. This process is not only expensive but also involves substantial disposal problems. Therefore, preparation from 3,3',5,5'-tetra-t-butyldiphenoquinone is preferred. For example, U.S. Pat. No. 3,631,208 describes a process for the preparation of 4,4'-dihydroxybiphenyl by the reduction of tetra-t-butyldiphenoquinone with 2,6-di-t-butylphenol in the presence of an amine, followed by dealkylation in the presence of an aluminum phenolate at temperatures of approximately 280° C. The intermediate 3,3',5,5'-tetra-t-butyl-4,4'-dihydroxybiphenyl is precipitated with a suitable precipitant and optionally recrystallized. A variation of this process is described in Russian Patent No. 1,011,626, in which the dealkylation is carried out in decalin, undecane, or tridecane in the presence of a trialkylphenolate.

U.S. Pat. No. 4,482,755 discloses the reduction of 3,3',5,5'-tetra-t-butyldiphenoquinone using a heterogeneous catalyst (for example, Pd/C). After separation, the product is dealkylated using an acidic ion exchanger. A drawback of this procedure is the formation of substantial amounts of by-products. The acid-catalyzed dealkylation can also be carried out with sulfuric acid (Japanese Patent Application No. 83/189,127 and U.S. Pat. No. 4,354,047) or p-toluenesulfonic acid in a suitable solvent (Japanese Patent Application No. 85/23,338 and U.S. Pat. No. 4,354,048).

Thus, according to the previously known processes, it is necessary to carry out the reaction in a solvent and to isolate the 3,3',5,5'-tetra-t-butyl-4,4'-dihydroxybiphenyl formed as an intermediate. Both steps are costly and hinder the availability of the target product.

SUMMARY OF THE INVENTION

Accordingly, it is an object of the present invention to provide a novel process for the preparation of 4,4'-dihydroxybiphenyl, which is economical and simple.

It is another object of the present invention to provide a novel process for the preparation of 4,4'-dihydroxybiphenyl that does not require a solvent.

It is a further object of the present invention to provide a process for the preparation of 4,4'-dihydroxybiphenyl which does not require recycling any auxiliary materials, such as pyridine.

It is still another object of the present invention to provide a process for the preparation of 4,4'-dihydroxybiphenyl which allows the efficient catalysis of the reaction of 3,3',5,5'-tetra-t-butyldiphenoquinone with 2,6-di-t-butylphenol.

It is still a further object of the present invention to provide a process for the preparation of 4,4'-dihydroxybiphenyl which does not require the isolation of any intermediate.

It is yet a further object of the present invention to provide a process for the preparation of 4,4'-dihydroxybiphenyl which does not produce any by-products and provides a product of high purity.

These and other objects which will become apparent during the course of the following detailed description have been achieved by the reduction, in the melt, of 3,3',5,5'-tetra-t-butyldiphenoquinone with 2,6-di-t-butylphenol in the presence of a catalytic amount of a 4-dialkylaminopyridine and the subsequent dealkylation, in the melt, of the intermediate 3,3',5,5'-tetra-t-butyl-4,4'-dihydroxybiphenyl by the addition of a substantially equimolar amount, based on the number of moles of 4-dialkylaminopyridine, of a phosphorus-containing acid or its derivative and heating, to obtain 4,4'-dihydroxybiphenyl. In the present process, no solvent is required, and the intermediate product does not need to be isolated.

DETAILED DESCRIPTION OF THE PREFERRED EMBODIMENT

The present process involves first reducing 3,3',5,5'-tetra-t-butyldiphenoquinone with 2,6-di-t-butylphenol in the presence of a catalytic amount of a 4-dialkylaminopyridine. The reaction is suitably carried out in the melt, preferably at a temperature of 240° to 280° C., more preferably 270° to 280° C. The 2,6-di-t-butylphenol is suitably added in an amount of 2 to 10 moles per mole of 3,3',5,5'-tetra-t-butyldiphenoquinone, preferably 2 to 3 moles per mole of 3,3',5,5'-tetra-t-butyldiphenoquinone. The 4-dialkylamino-pyridine is suitably added in an amount of 0.003 to 0.02 mole per mole of 3,3',5,5'-tetra-t-butyldiphenoquinone.

The subsequent dealkylation of the present process is carried out by adding a phosphorus-containing acid or derivative thereof in a substantially equimolar amount to the 4-dialkylaminopyridine. The dealkylation is suitably carried out in the melt at a temperature of 280° to 320° C., preferably 300° to 320° C.

Thus, the process of the present invention may involve first heating a mixture of 3,3',5,5'-tetra-t-butyldiphenoquinone, 2,6-di-t-butylphenol, and a 4-dialkylaminopyridine to a temperature of 240° to 280° C. It is also possible to add the 4-dialkylaminopyridine only at the higher temperatures. However, this provides no benefit. Fading of the color of the reaction mixture indicates that the reduction is complete. After the reduction is complete, any excess 2,6-di-t-butylphenol is distilled as quantitatively as possible. It is preferred to raise the temperature of the reaction mixture briefly to about 280° C. for this purpose.

The subsequent dealkylation is suitably carried out by adding a phosphorus-containing compound to the reaction mixture at a temperature of 240° C. and slowly raising the temperature until the evolution of gas stops. The evolution of gas is ordinarily complete at a temperature of about 320° C.

The product can be isolated by any conventional isolation technique, for example, by sublimation or recrystallization.

Suitable 4-dialkylaminopyridines for the present process have the formula:

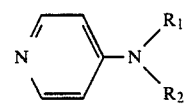

In this formula, $R_1$ and $R_2$, independently of one another, are alkyl groups with 1 to 6 carbon atoms, or in combination with the nitrogen atom to which they are bonded form a pyrrolidine or piperidine ring. Preferred 4-dialkylaminopyridines are 4-dimethylaminopyridine, 4-di-n-butylaminopyridine, 4-di-n-hexylaminopyridine, or 4-piperidinylpyridine.

Suitable catalysts for the dealkylation step are phosphorus-containing acids and their derivatives such as phosphorus-containing acid esters and phosphorus-containing acid salts. Preferred phosphorus-containing acids have the general formula $H_3PO_n$ with n=2, 3, or 4.

The present process is advantageous over those of the prior art, because no solvent is required. In addition, costly recycling steps to recover the previously required auxiliary materials, such as pyridine, can be omitted. The present process also allows for efficient catalysis in the reaction of the 3,3',5,5'-tetra t-butyldiphenoquinone with 2,6-di-t-butylphenol and removes the necessity of isolating an intermediate. Furthermore, since the 3,3',5,5'-tetra-t-butyldiphenoquinone and 2,6-di-t-butylphenol both form the same intermediate product, there is no formation of by-products and a final product of high purity is obtained. Other features of the present invention will become apparent in the course of the following descriptions of exemplary embodiments which are given for illustration and are not intended to be limiting thereof.

EXAMPLES

Example 1

28.6 g (70 mmoles) of 3,3',5,5'-tetra-t-butyldiphenoquinone, 29 g (140 mmoles) of 2,6-di-t-butylphenol, and 0.25 g (1.2 mmole) of 4-dibutylaminopyridine are heated under nitrogen at 255° C. The reaction mixture loses its color after 30 minutes and is then treated with 0.16 g (1.2 mmoles) of hypophosphorous acid (50%) and the temperature is slowly raised to 300° C. After the completion of gas evolution, the product is obtained by sublimation at 1 mbar and 300° C.

Yield: 24.8 g (>95%)
M.p.: 278°–280° C.

Example 2

28.6 g (70 mmoles) of 3,3',5,5'-tetra-t-butyldiphenoquinone, 57.8 g (280 mmoles) of 2,6-di-t-butylphenol, and 0.04 g (0.33 mmole) of 4-dimethylaminopyridine are heated under nitrogen at 260° C. The reaction mixture, which loses its color after 30 minutes, is heated to 280° C., and the excess 2,6-di-t-butylphenol is distilled off. The melt is then treated with 0.03 g (0.33 mmole) of phosphorous acid at 250° C. Heating to 280° C. leads to the evolution of isobutene and the formation of the light beige product, which is recrystallized from ethanol.

Yield: 23.9 g (>90%)
M.p.: 278°–280° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of 4,4'-dihydroxybiphenyl, comprising the steps:
   (i) reducing 3,3',5,5'-tetra-t-butyldiphenoquinone with 2,6-di-t-butylphenol in the presence of a 4-dialkylaminopyridine of the formula

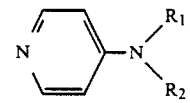

wherein $R_1$ and $R_2$, independently of one another, are an alkyl group with 1 to 6 carbon atoms, or $R_1$ and $R_2$ together with the nitrogen atom to which they are bonded form a pyrrolidine or piperidine ring, to obtain 3,3',5,5'-tetra-t-butyl-4,4'-dihydroxybiphenyl; and
   (ii) dealkylating said 3,3',5,5'-tetra-t-butyl-4,4'-dihydroxybiphenyl in the presence of a phosphorus-containing acid; wherein said reducing and said dealkylating are carried out in the melt, wherein said phosphorus-containing acid has the formula $H_3PO_n$ with n=2, 3, or 4, wherein 2 to 10 moles of said 2,6-di-t-butylphenol, 0.003 to 0.02 moles of said 4-dialkylaminopyridine, and 0.003 to 0.02 moles of said phosphorus-containing acid are used per mole of said 3,3',5,5'-tetra-t-butyldiphenoquinone, and wherein said reducing is carried out at a temperature of 240° to 280° C., and said dealkylating is carried out at a temperature of 280° to 320° C.

2. The process of claim 1, wherein said 4-dialkylaminopyridine is one member selected from the group consisting of 4-dimethylaminopyridine, 4-di-n-butylaminopyridine, 4-di-n-hexylaminopyridine, and 4-piperidinylpyridine.

3. The process of claim 1, wherein 2 to 3 moles of said 2,6-di-t-butylphenol are used per mole of said 3,3',5,5'-tetra-t-butyldiphenoquinone.

4. The process of claim 1, wherein said reducing is carried out at a temperature of 270° to 280° C. and said dealkylating is carried out at a temperature of 300° to 320° C.

5. The process of claim 1, wherein said phosphorus-containing acid or derivative thereof is added in an amount substantially equimolar to said 4-dialkylaminopyridine.

6. The process of claim 1, wherein said phosphorus-containing acid or derivative thereof is selected from the group consisting of phosphorus-containing acid esters and phosphorus-containing acid salts.

* * * * *